(12) United States Patent  
Choromanski et al.

(10) Patent No.: US 7,462,359 B2  
(45) Date of Patent: Dec. 9, 2008

(54) NEOSPORA VACCINES

(75) Inventors: Leszek J. Choromanski, Lenexa, KS (US); Karen K. Brown, Parkville, MO (US)

(73) Assignee: Intervet International B.V., Boxmeer (NL)

(*) Notice: Subject to any disclaimer, the term of this patent is extended or adjusted under 35 U.S.C. 154(b) by 147 days.

(21) Appl. No.: 11/119,474

(22) Filed: Apr. 28, 2005

(65) Prior Publication Data

US 2005/0186227 A1 Aug. 25, 2005

Related U.S. Application Data

(62) Division of application No. 10/115,478, filed on Apr. 2, 2002, now abandoned, which is a division of application No. 08/954,531, filed on Oct. 20, 1997, now abandoned.

(51) Int. Cl.
  *A61K 39/02* (2006.01)
(52) U.S. Cl. .............. 424/269.1; 424/151.1; 424/184.1; 424/265.1; 424/193.1
(58) Field of Classification Search .............. 424/151.1, 424/184.1, 269.1, 265.1, 193.1
  See application file for complete search history.

(56) References Cited

U.S. PATENT DOCUMENTS

| 4,582,798 | A | 4/1986 | Brown et al. |
| 5,583,014 | A | 12/1996 | Brown et al. |
| 5,707,617 | A | 1/1998 | Conrad et al. |
| 5,766,602 | A | 6/1998 | Xiong et al. |
| 5,889,166 | A | 3/1999 | Conrad et al. |
| 6,071,737 | A | 6/2000 | Marsh et al. |
| 6,787,146 | B2 | 9/2004 | Brake et al. |

FOREIGN PATENT DOCUMENTS

| EP | 0 764 446 A2 | 3/1997 |
| EP | 0 841 392 A2 | 5/1998 |
| WO | WO 95 25541 | 9/1995 |
| WO | WO 97 39009 | 10/1997 |
| WO | WO 99 20303 | 4/1999 |
| WO | WO 99 47927 | 9/1999 |

OTHER PUBLICATIONS

Anderson, M. et al. "Protozoal Causes of Reproductive Failure in Domestic Ruminants" Veterinary Clinics of North America: Food Animal Practice (Nov. 1994) V10, N3, p. 439-461.

Anderson, M. et al. "Neospora-like protozoan infection as a major cause of abortion in . . . " JAVMA, (Jan. 15, 1991) V198, N2, p. 241-244.

Anderson, M. et al. "Evidence of vertical transmission of *Neospora sp* infection in dairy cattle" JAVMA (Apr. 15, 1997) V210, N8, p. 1169-1172.

Andrianarivo, A.G. et al. "Immunogenicity of a killed whole *Neospora caninum* . . . " International J. Parasitology 29 (1999) p. 1613-1625.

Barber, J. S. et al. Characterization of the first European isolate of *Neospora caninum* (Dubey, Carpenter, Speer, Topper and Uggla) Parasitology (1995), 111, p. 563-568.

Barr, B.C., et al. "Experimental reproduction of bovine fetal Neospora infection and death with a bovine . . . " J. Vet Diagnostic Investigation, (Apr. 1994) V6, N2, p. 207-215.

Barta, J.R. et al. "Characterzation of anti-*Neospora caninum* hyperimmune rabbit serum by Western blot analysis and . . . " Parasitology Research (1992) V78, p. 689-694.

Baszler, T.V., et al. "Serological Diagnosis of Bovine Neosporosis by *Neospora caninum* . . . " J. of Clinical Microbiology (Jun. 1996) V34, N6, p. 1423-1428.

Bjorkman, C., et al. "Characterization of *Neospora caninum* miscom antigens using monoclonal antibodies" Parasite Immunology (Feb. 1998) V20, N2, p. 73-80.

Buxton, D. "Protozoan infections (*Toxoplasma gondii*, *Neospora caninum* and *Sarcocystis spp.*) in sheep and goats:recent advances" Vet. Res. (1998) 29, 289-310.

Cuddon, P. et al. "*Neospora caninum* infection in English Springer Spaniel Littermates Diagnostic Evaluation and . . . " J. of Veterinary Internal Medicine (1992) V6, N6, p. 325-332.

Dubey, J.P. et al. "Antibody responses of cows during an outbreak of neosporosis evaluated by indirect fluorescent . . . " J. of Parasitology (Dec. 1997) V83, N6, p. 1063-1069.

Dubey, J.P. et al. "Newly recognized fatal protozoan disease of dogs" JAVMA (May 1998) V192, N9, p. 1269-1285.

Dubey, J.P. "Recent advances in Neospora and neosporosis" Veterinary Parasitology (1999) V84, p. 349-367.

Dubey, J.P. et al. "A review of *Neospora caninum* and neosporosis" Veterinary Parasitology (1996) V67, p. 1-59.

Hemphill, A. et al. "The antigenic composition of *Neospora caninum*" International Journal for Parasitology (1999) V29, p. 1175-1188.

Hemphill, A. "The Host-Parasite Relationship in Neosporosis" Advances in Parasitology (1999) V43, p. 47-104.

Ho, Michael S.Y., et al. "Detection of *Neospora SP*, from infected Bovine Tissues by PCR and Probe Hybridization" The Journal of Parasitology (Jun. 1997) V83, N3, p. 508-514.

Howe, D.K., et al "Comparison of the major antigens of *Neospora caninum* and *Toxoplasma gondii*" International Journal forParasitology (1999) V29, p. 1489-1496.

Jenkins, M.C., et al. "Serological Response over Time to Recombinant *Neospora caninum* Antigens in . . . " Clinical and Diagnostic Laboratory Immunology (May 1997) V4, N3, p. 270-274.

Kasper, L.H. et al. "Antigen-Specific CD8+ T Cells Protect against Lethal Toxoplasmosis in Mice Infected with *Neospora* . . . " Infection and Immunity (Apr. 1998) V66, N4, p. 1554-1560.

(Continued)

*Primary Examiner*—Jennifer E Graser
(74) *Attorney, Agent, or Firm*—William M. Blackstone

(57) ABSTRACT

A *Neospora caninum* vaccine comprising tissue culture grown *Neospora* and methods of making and using said vaccines. *Neospora caninum* vaccines described include those containing whole *Neospora* tachyzoites, extracts of *Neospora* tachyzoites and protective antigen subunits of *Neospora* tachyzoites. The vaccines of this invention may be in a liquid or lyophilized form.

6 Claims, No Drawings

OTHER PUBLICATIONS

Lally, N. et al. "Identification of *Neospora caninum* cDNA clones expressing recombinant antigens . . . " Am. J. Trop. Med. Hyg. Abstract 53/2 p. 288.

Lally,N. et al. "Evaluation of Two *Neospora caninum* Recombinant Antigens for use in an Enzyme-Link . . . " Clinical and Diagnostic Laboratory Immunology (May 1996) V3, N3, p. 275-279.

Lindsay, D.S. et al. "Vaccination of Mice with *Neospora caninum*: Response to oral challenge with *Toxoplasma gondii* Oocysts" The J. of Parasit. (Apr. 1998) V84, N2, p. 311-315.

Lindsay, D.S., et al. "Infection of Mice with *Neospora caninum* (Protozoa: Apicomplexa) Does Not Protect against . . . " Infection and Immunity (Aug. 1990) V58, N8, p. 2699-2700.

McAllister, M. et al. "Ingestion of *Neospora caninum* tissue cysts . . . " International Journal for Parasitology (1999) 29 p. 1531-1536.

McGuire, A. et al. "Experimental inoculation of domestic pigeons . . . " International Journal for Parasitology (1999) 29 p. 1525-1529.

Marks, J. et al. "Identification of Neospora antigens recognized by CD4+ immune sera from experimentally infected cattle" Parasite Immunology (1998) V20,N7, p.303-309.

Nishikawa, Y. et al. "Monoclonal anitbody inhibition of *Neospora caninum* techyzoite . . . " International Journal for Parasitology 30 (2000) 51-58.

NEOSPORA VACCINES

RELATED APPLICATIONS

This application is a divisional application of application Ser. No. 10/115,478 filed Apr. 2, 2002, now abandoned, which in turn is a divisional application of application Ser. No. 08/954,531 filed Oct. 20, 1997 and now abandoned.

BACKGROUND OF THE INVENTION

1. Field of the Invention

The present invention relates to a vaccine for protection of mammals from disease caused by *Neospora caninum*. More specifically, the invention relates to safe and immunogenically effective vaccines for protection of bovines and canines from abortion caused by *Neospora caninum*.

2. Brief Description of the Prior Art

*Neospora caninum* was first reported by Dubey et al (JAVMA, Vol. 192, No. 9, May 1, 1988) as a Toxoplasmosis-like illness affecting dogs. *Neospora caninum* was found to be structurally distinct from *Toxoplasma gondii* and did not react with anti-*T. gondii* antiserum in an immunoperoxidase test. Dubey et al described the major lesions associated with the organism as meningoencephalomyelitis and myositis. Within the past few years, neosporosis has become recognized as a major reproductive disease in cattle (Anderson et al., 1994, Food Animal Practice, 10: 439-461) with cases reported in North and South America, Europe, Africa, the Pacific-rim countries as well as in the United States. The major clinical manifestation of bovine neosporosis is fetal abortion, with focal nonsuppurative necrotizing encephalitis, nonsuppurative myocarditis, and myositis in the fetus (Anderson et al., 1991, Journal of the American Veterinary Medical Association, 198: 241-244). According to Anderson et al., 1997 (Journal of the Veterinary Medical Association, 210: 1169-1172), retrospective studies of cattle in California indicate that neosporosis has been endemic since at least 1985. These authors state that 18 to 19% of all aborted bovine fetuses submitted to the California Veterinary Diagnostic Laboratory System have *Neospora* sp infection. In a prospective survey of selected dairies in California, the number of abortions attributed to *Neospora* sp infections was even greater (42.5%).

Ho et al (J. Parasitol., 1997, 83(3)) have recently reported the successful reproduction of bovine abortion and fetal infection by infecting pregnant cows with tachyzoites of *Neospora caninum*. This publication suggests that there may be a correlation between serological titer as measured by indirect fluorescent antibody (IFA) testing and protection from abortion caused by *Neospora caninum* in cows. Cows with IFA titers of 320 and 640 did not abort after infection with tachyzoites of this organism.

As mentioned previously, neosporosis has also been reported in puppies and in dogs as old as 15 years of age. The percentage of infected dogs that show clinical signs is unknown. In dogs, *Neospora caninum* can infect any tissue, although it is most commonly found in the central nervous system and spinal nerve roots. The most severe infections are seen in puppies that were infected in utero. These puppies exhibit ascending paralysis. Abortion can be reproduced in experimental infection of pregnant bitches during the early stage of gestation. Sulfonamides, pyrimethamine and clindamycin have been used to treat neosporosis in dogs.

*Neospora caninum* can also produce a fatal infection in experimentally inoculated cats. However, the disease has not yet been reported to occur naturally in cats.

Neosporosis has been observed to cause abortion in sheep and goats but to a lesser extent than is found in cattle. Experimental infection is readily induced in sheep and goats by subcutaneous injection of tachyzoites.

Although neosporosis, especially in cattle, appears to pose an increasingly serious problem and there is certainly a long felt need to solve this problem by protecting mammals using a vaccine, there are no descriptions of vaccines, vaccine development nor suggestions of methods of preparing vaccines to protect cattle and other animals from disease caused by *Neospora caninum*.

SUMMARY OF THE INVENTION

It is a focus of this invention to describe a vaccine composition for protection of mammals from disease caused by *Neospora caninum* comprising tissue culture grown *Neospora caninum* tachyzoites as a whole culture or in an extract form or as subunit antigens obtained therefrom. In addition, it is a focus of this invention to describe a method of producing a vaccine for protection of mammals from disease caused by *Neospora caninum* comprising the steps of: growing *Neospora caninum* in a susceptible tissue culture until a cytopathic effect (CPE) is produced, harvesting said tissue culture grown *Neospora caninum* and formulating said harvest into a vaccine. A modified live vaccine produced in this manner can be administered to mammals without inactivating the *Neospora* sp. However, said non-inactivated *Neospora* sp would need to be attenuated by art-known techniques prior to growing it in tissue culture. Another method of producing a vaccine for protection of mammals from disease caused by *Neospora caninum* comprises the steps of: 1) growing *Neospora caninum* in a susceptible tissue culture until a CPE is produced; 2) harvesting said tissue culture grown *Neospora caninum*; 3) inactivating said harvested tissue culture grown *Neospora caninum*; and 4) adjuvanting the inactivated harvested tissue culture grown *Neospora caninum* to produce a vaccine. Still another method of producing a vaccine for protection of mammals from disease caused by *Neospora caninum* comprises the steps of: 1) growing *Neospora caninum* in a susceptible tissue culture until a CPE is produced; 2) harvesting said tissue culture grown *Neospora caninum*; 3) extracting protective antigens from the harvested tissue culture grown *Neospora caninum* to produce subunits; 4) inactivating the subunits if necessary; and 5) adjuvanting the subunits to produce a vaccine. It is within the scope of this invention to inactivate the *Neospora caninum* prior to extraction of the protective antigen subunits

DETAILED DESCRIPTION OF INVENTION

As set forth above, the present invention is directed to vaccine compositions comprising a modified live *Neospora caninum* grown in a susceptible tissue culture or an inactivated, adjuvanted *Neospora caninum* grown in a susceptible tissue culture or subunits derived from *Neospora caninum*. The method of producing the above vaccine compositions comprises growing *Neospora caninum* under artificial conditions, in tissue culture, for the purpose of obtaining parasite antigens for use in vaccines. The *Neospora caninum* can be obtained from any source. It is preferred that a vaccine for bovines contain a *Neospora caninum* isolated from an aborted bovine fetus. Additionally, it is preferred that a vaccine intended for canines contain a *Neospora caninum* isolated from a canine. Illustratively, the brain of an infected fetus is harvested, homogenized in a growth medium such as Minimal Essential Media (MEM) or in a diluent such as phosphate buffered saline (PBS) supplemented with antibiotics to minimize the potential for contamination. Such a homogenate is centrifuged to remove the large particulate matter and the supernate is inoculated onto various tissue cultures and passaged in tissue cultures, if necessary, until a cytopathic effect (CPE) is produced on at least one tissue culture. The tissue culture is preferably a cell line in which the parasite grows to a high titer so that a Master Seed can be prepared. A high titer means that the parasite tachyzoites grow to produce a count, as visualized under a microscope, or a titer when placed back into tissue culture of at least $1\times10^4$ tissue culture infective dose$_{50}$/mL (TCID$_{50}$/mL). Preferably, $1\times10^5$ TCID$_{50}$/mL are produced and more preferably, $1\times10^6$ TCID$_{50}$/mL are produced. A Master Seed means that the tissue culture grown *Neospora* sp is grown to a high titer, aliquoted into equivalent volumes in freezing vials and frozen, after which it is tested for freedom from contaminants (bacteria, fungi and viruses) and then used to prepare Working Seeds and Production Seeds. Working Seeds and Production Seeds mean further passage of the Master Seed in a susceptible tissue culture, aliquoting, freezing and repeat testing so that vaccines can be produced from the Production Seeds instead of using the Master Seed and all vaccine is prepared from the same origin material. A susceptible tissue culture means a tissue culture that, when inoculated with *Neospora* sp, is able to grow the parasite tachyzoites and produce CPE.

At least three types of vaccines can be made according to this invention, a modified live vaccine, an inactivated vaccine or a subunit vaccine. If a modified live vaccine is to be made, the *Neospora* sp must be mutated or genetically modified so that the parasite loses its virulence, by art-known techniques including but not limited to chemical mutagenesis and genetic engineering, prior to making the Master Seed. Once the non-virulent (avirulent) mutant is prepared, a Master Seed is made by growing the mutated *Neospora* sp in a susceptible tissue culture and frozen as described above. Preparation of a modified live vaccine comprises the steps of growing the mutated *Neospora caninum* in a susceptible tissue culture until CPE is produced, harvesting the tissue culture grown *Neospora* sp and formulating said harvest into a vaccine. Formulation may include addition of stabilizers and/or adjuvants or immunomodulators. The vaccine may remain in a liquid form or may be lyophilized.

The method for preparation of an inactivated *Neospora caninum* vaccine requires that the organism be grown to higher titer and comprises the steps of growing *Neospora caninum* in a susceptible tissue culture until a CPE is produced, harvesting said tissue culture grown *Neospora caninum*, inactivating said harvested tissue culture grown *Neospora caninum*; and adjuvanting the inactivated harvested tissue culture grown *Neospora caninum* to produce a vaccine.

The method for preparation of a subunit *Neospora caninum* vaccine comprises the steps of growing *Neospora caninum* in a susceptible tissue culture until a CPE is produced, harvesting said tissue culture grown *Neospora caninum*, extracting protective antigens from the harvested tissue culture grown *Neospora caninum* to produce protective antigen subunits, inactivating the subunits if necessary; and adjuvanting the subunits to produce a vaccine. It is within the scope of this invention to inactivate the *Neospora caninum* prior to extraction of the protective antigen subunits in order to prepare a subunit vaccine.

Inactivating agents may be selected from the group consisting of formalin, beta-propiolactone (BPL), heat, binary ethylenimine (BEI), detergents and freeze/thaw with the preferred inactivating agents being BEI and BPL.

Adjuvants used to increase the immunogenicity of the *Neospora* vaccines of this invention may be selected from the group consisting of polymers such as Carbopol, HAVLOGEN® and POLYGEN®, oil in water such as EMULSIGEN® and EMULSIGEN PLUS®, water-in-oil-in-water, aluminum hydroxide, aluminum phosphate, aluminum sulfate, immuno-modulators such as BAYPAMUN®, lipid based adjuvants such as Bay R-1005 and liposomes and combinations thereof.

The inactivated *Neospora* vaccines of this invention may include stabilizers which are added before or after adjuvanting in order to maintain the antigen content over long periods of time and under adverse conditions of high or low temperatures. Stabilizers are selected from the group consisting of protease inhibitors, sugars such as sucrose and glycerol, encapsulating polymers, chelating agents such as ethylene-diaminetetracetic acid (EDTA), proteins and polypeptides such as gelatin and polyglycine and combinations thereof.

The examples to follow represent compositions of *Neospora caninum* vaccines and describe their methods of production including growing the tachyzoites of this organism in such diverse cell lines as an Equine Dermal cell line (ATCC No.CCL-57), a Vero cell line and an African Green Monkey kidney cell line (BIOWHITTAKER No. 75-104) which was cloned at Bayer Corporation to produce a cell line designated MA 104 Clone B as well as describing their use in vaccinating bovines to produce protective indirect fluorescent antibody (IFA) titers.

The invention is further illustrated but is not intended to be limited by the following examples in which all parts and percentages are by weight unless otherwise specified.

EXAMPLES

Example 1

In order to determine whether *Neospora caninum* vaccines can produce protection against abortion in pregnant cows in a model known in the art (Ho et al., 1997), the inventors produced *Neospora caninum* vaccines by growing the *Neospora caninum* on a Vero cell line in 850 cm$^2$ roller bottles. A vial of Working Cells of the Vero cell line was removed from liquid nitrogen storage, thawed rapidly, diluted and placed into 850 cm$^2$ roller bottles containing 250 mL of DMEM (high glucose), hereinafter designated DMEMH, at a rate of $4\times10^7$ cells per roller. The medium was supplemented with Neomycin Sulfate at 1 mL/L and Horse Serum at 5% v/v. Cells were incubated at 36 to 38° C. for 5 to 7 days until the cells were between 95 and 100% confluent. The Working Cells were removed from the roller bottles by rinsing the cell sheet with Phosphate Buffered Saline (PBS) and then adding 10 mL of a Trypsin-Ethylene-diaminetetracetic acid disodium salt (EDTA) solution (2.5 g/L of Trypsin +1 g/L EDTA) to each roller bottle, agitating the bottles gently for at least 10 minutes until the cells slough from the surface and then rinsing the bottle surface with DMEMH and pooling the contents of all of the bottles. The cells from these bottles (Production Cells) were re-inoculated into new 850 cm$^2$ roller bottles at $4.5\times10^7$ cells per roller bottle. The Production Cells were incubated for 24 hours at 36 to 38° C. after which they were infected with freshly-passaged *Neospora caninum* tachyzoites of Strain BPA-1 ($3\times10^8$ to $4.5\times10^8$/850 cm$^2$ roller bottle). At the time of infection, the production cells were at least 50% confluent. Infected roller bottles were incubated at 36 to 38° C. for 120 to 168 hours on rotating roller racks set at between 0.2 and 0.4 rpm. At that time, the cell sheet was displaying typical CPE affecting at least 80% of the cell sheet. At the end of the incubation period the *Neospora* fluids were harvested by pooling the contents from all of the roller bottles into a sterile vessel and a sample was removed for live *Neospora* titration. Acceptable harvest fluids must have a titer of at least $3\times10^5$/mL. The harvest titer for the present batch was $3\times10^5$/mL. The harvest fluids were frozen and thawed twice by holding the harvest fluids at $-70°$ C. and thawing them rapidly at temperatures no higher than $37°$ C. After this treatment, the harvest fluids were inactivated for a period of 48 hours at $4°$ C. with 0.2 M Binary Ethylenimine (BEI). After inactivation, the BEI was neutralized with 3.16 M sodium thiosulfate. The inactivated harvest fluids were concentrated by centrifugation at 3500 rpm for 15 minutes and the pellet was re-suspended in PBS to a concentration of $3.0\times10^7$ based on a microscopic count. Aliquots of these inactivated and concentrated harvest fluids were adjuvanted with two different types of adjuvants in order to prepare two different vaccine formulations. One half of the inactivated and concentrated harvest fluids was adjuvanted with 10% (v/v) HAVLOGEN® while the remainder of the inactivated concentrated harvest fluid was adjuvanted with 15% (v/v) of EMULSIGEN®. HAVLOGEN® is a polymer based adjuvant containing Carbopol while EMULSIGEN® is an oil-in-water based adjuvant.

The two vaccine formulations were used to vaccinate heifers ranging in age from two to two and one-half years of age. All heifers were bred and when pregnancy was confirmed at $30\pm5$ days, these animals were divided into four groups which were treated as follows:

Group 1 heifers (No. 21, 30, 39 and 20) were injected subcutaneously two times at 4 week intervals with a *Neospora* vaccine containing 10% HAVLOGEN® adjuvant.

Group 2 heifers (No. 18, 37, 40 and 431) were injected subcutaneously two times at 4 week intervals with a *Neospora* vaccine containing 15% EMULSIGEN®.

Group 3 heifers (No. 429, 25, 28 and 2) served as controls and were injected subcutaneously two times at 4 week intervals with a control preparation containing only uninfected Vero cell cultures containing 15% EMULSIGEN®.

Group 4 heifers (No. 19, 10, 4, and 14) served as contact controls and were neither vaccinated nor challenged.

Serum samples from all heifers were taken at least one week prior to vaccination (P.V.), on the day of first vaccination (day 0) and on Weeks 5, 6 and 7 post vaccination, on the day of booster (boost), the day of challenge (between Week 11 and 12, and weekly thereafter through Week 16 post vaccination. All heifers started the study as seronegative. Only the titers measured on the day of challenge are listed in Table 1 as these are the most titers for this study.

Heifers from Groups 1-3 were challenged with $8\times10^7$ virulent *Neospora caninum* tachyzoites of strain BPA-1 grown in Vero cells. Challenge occurred at $85\pm5$ days of gestation. Fetuses were removed by caesarian section from the heifers at $40\pm6$ days (114 to 120 days) of gestation and evaluated by gross examination. The presence of dead fetuses were interpreted to indicate that the vaccine did not protect the fetuses and would have resulted in abortion of the fetuses. The presence of live fetuses was interpreted as demonstrating protection of the fetuses and that abortion should not have occurred.

Table 1 shows the results of the fetal evaluation and lists the serological titers of the heifers on the day of challenge. The results shown in this table indicate that the heifers in Group 1 contained two live fetuses and two dead fetuses suggesting that the HAVLOGEN® adjuvanted *Neospora* vaccine produced 50% protection from abortion. It should be noted that the two protected heifers had titers at challenge of 320 and 640 respectively. The heifers in Group 2 vaccinated with EMULSIGEN® adjuvanted *Neospora* vaccine contained one live fetus from a heifer with a serological titer of 320. The remaining heifers in this vaccine group had dead fetuses and titers lower than 320 at challenge. The first two heifers in Group 3 (Control Group receiving adjuvanted Vero cells without *Neospora*) had dead fetuses and titers <80. The remaining two heifers in this group were challenged at a later time than all of the other heifers and it is proposed that they did not receive a high enough challenge dose and, therefore, had live fetuses. Their titers were <80 on the day of challenge and at a later histological examination it was shown that these heifers were not infected. Group 4 heifers did not develop antibody titers during the study indicating that the other groups did not shed *Neospora* organisms. This latter group was not challenged since they only served as contact controls.

This experiment supports the inventor's interpretation of the Ho et al data wherein the inventors proposed that a 320 IFA titer might be indicative of protection from fetal abortion.

TABLE 1

Results of Fetal Evaluation Post Challenge with Virulent Neospora BPA-1

| Group | Heifer No. | Gestational Age at Removal of Fetus | Appearance of Fetus at Removal | Titer of Heifer at Challenge |
|---|---|---|---|---|
| 1 HAV | 21 | 119 days | LIVE | 320 |
| 1 HAV | 30 | 119 days | DEAD | 160 |
| 1 HAV | 39 | 114 days | LIVE | 640 |
| 1 HAV | 20 | 120 days | DEAD | 160 |
| 2 EMUL | 18 | 119 days | DEAD | 160 |
| 2 EMUL | 37 | 119 days | DEAD | 160 |
| 2 EMUL | 40 | 118 days | LIVE | 320 |
| 2 EMUL | 431 | 111 days | DEAD | 160 |
| Controls | 429 | 118 days | DEAD | <80 |
|  | 25 | 114 days | DEAD | <80 |
| Controls | 28 | 120 days | LIVE/NI* | <80 |
|  | 2 | 120 days | LIVE/NI* | <80 |
| Contact | 19 | 121 days | LIVE | <80 |
| Controls | 10 | 121 days | LIVE | <80 |
| Contact | 4 | 120 days | LIVE | <80 |
| Controls | 14 | 120 days | LIVE | <80 |

HAV = HAVLOGEN ®
EMUL = EMULSIGEN ®
*NI = Not Infected as determined by later histopathology Example 2

This experiment was conducted in order to determine whether a *Neospora caninum* organism could be grown in another tissue culture cell line, inactivated and formulated to prepare a vaccine which could produce antibody titers in cattle which would be similar to those observed in EXAMPLE 1 with *Neospora* vaccines produced on a Vero cell line.

An Equine Dermal Cell Line, Master Cell Passage 11, derived from ATCC No. CCL-57 was diluted to a cell count of $2\times10^7$ cells per roller bottle in a Dulbecco's Modified Eagles Medium (DMEM) containing 10% Horse Serum and inoculated into 850 cm² roller bottles at a volume of 250 mL per roller bottle. The cells were grown to confluency after which they were infected with $2.4\times10^7$ *Neospora caninum* tachyzoites in 14.1 mL of DMEM. Each roller bottle contained 264 mL of DMEM plus 10% Horse Serum. The *neospora*-infected tissue cultures were incubated at $37°$ C. until at least 50% of the cells demonstrated CPE (approximately 7 to 9 days). Fluids were harvested and tachyzoites were centrifuged for 30 minutes at 3500 rpm in order to concentrate the harvested antigen. The pelleted concentrated *Neospora caninum* antigen was re-suspended in 200 mL of decanted DMEM supernatant from the centrifuged tachyzoites. This concentrated preparation containing $8 \times 10^6$ tachyzoites per mL was frozen for 16 hours at −70° C. and then thawed at room temperature. The preparation was then inactivated using 0.05 M binary ethylenimine (BEI) incubated at 4° C. for 48 hours. The inactivated preparation was neutralized using 3.16 M sodium thiosulfate. Two equal aliquots of the inactivated, neutralized *Neospora caninum* antigen preparation were then adjuvanted with different adjuvants as in EXAMPLE 1. One half of the preparation was adjuvanted with HAVLOGEN®, a Carbopol-based polymer adjuvant, by adding adjuvant to a 10% concentration (v/v). The other half of the preparation was adjuvanted with EMULSIGEN®, an oil-based adjuvant, by adding adjuvant to a 15% concentration (v/v).

The adjuvanted *Neospora caninum* vaccines produced on Equine Dermal Cells were injected subcutaneously into calves ranging in age from 9 to 12 months. One calf (#954) received a 5.0 mL dose of the HAVLOGEN® adjuvanted vaccine while a second calf (#955) received a 5.0 mL dose of EMULSIGEN® adjuvanted vaccine. Each calf was boostered with the homologous vaccine 10 days later. Calves were bled at each vaccination and 10 days post booster vaccination. Serum was analyzed for titer using an indirect fluorescent antibody (IFA) test. Serological titers of these calves are shown in Table 2. These results indicate that the EMULSIGEN® adjuvanted *Neospora* vaccine produced protective titers while the HAVLOGEN® adjuvanted *Neospora* vaccine produced a lower titer which was close to protective.

TABLE 2

Antibody Titers of Calves Vaccinated with inactivated adjuvanted *Neospora caninum* vaccines grown in Equine Dermal Cells

| VACCINE ADJUVANT | SERUM DAY 0 | ANTIBODY DAY 14 | TITER (IFA) DAY 24 |
|---|---|---|---|
| HAVLOGEN ® | <80 | 80 | 160 |
| EMULSIGEN ® | <80 | 80 | 2580 |

Example 3

After noting from EXAMPLES 1 and 2 that a *Neospora caninum* vaccine produced in a continuous cell line could produce protective antibody titers in cattle which correlated to protection from abortion, it was the object of this experiment to evaluate the effect of growing the *Neospora caninum* in a totally different cloned cell line derived from African Green Monkey Kidneys (MA-104 Clone B) and evaluating the effects of several different types of adjuvants on production of antibody titers in cattle.

A *Neospora caninum* vaccine was produced as follows. A vial of Working Cells (MA-104 Clone B horse serum) was removed from liquid nitrogen storage, thawed rapidly, diluted and inoculated into 850 cm² roller bottles containing 250 mL of DMEM (high glucose), hereinafter designated DMEMH, at a concentration of $4 \times 10^7$ cells per roller. The medium was supplemented with Neomycin Sulfate at 1 mL/L and Horse Serum at 5% v/v. Cells were incubated at 36 to 38° C. for 5 to 7 days until the cells were between 95 and 100% confluent. The Working Cells were removed from the roller bottles by rinsing the cell sheet with Phosphate Buffered Saline (PBS) and then adding 10 mL of a Trypsin-EDTA) solution (2.5 g/L of Trypsin +1 g/L EDTA) to each roller bottle, agitating the bottles gently for at least 10 minutes until the cells slough from the surface and then rinsing the bottle surface with DMEMH and pooling the contents of all of the bottles. The cells from these bottles (Production Cells) were re-inoculated into new 850 cm² roller bottles at $4.5 \times 10^7$ cells per roller bottle. The Production Cells were incubated for 24 hours at 36 to 38° C. after which they were infected with freshly-passaged *Neospora caninum* tachyzoites ($1.2 \times 10^7$/850 cm² roller bottle). At the time of infection, the production cells were at least 50% confluent. Infected roller bottles were incubated at 36-38° C. for 120 to 168 hours on rotating roller racks set at between 0.2 and 0.4 rpm. At that time, the cell sheet was displaying typical CPE affecting at least 50% of the cell sheet. At the end of the incubation period, the *Neospora* fluids were harvested by pooling the contents from all of the roller bottles into a sterile vessel from which a sample was removed for live *Neospora* tachyzoite titration. Acceptable harvest fluids must have a titer of at least $3 \times 10^5$/mL. The harvest titer for the present batch was $2.3 \times 10^6$. In this case the harvest fluids were concentrated by centrifugation in order to obtain $2.4 \times 10^7$ tachyzoites/mL. Other concentration methods include but are not limited to ultrafiltration and column chromatography. The harvest fluids were inactivated by addition of 0.2 M binary ethylenimine (BEI) to a final concentration of 0.01 M and incubation at 2 to 7° C. for at least 96 hours. After this incubation, the BEI was neutralized by addition of 3.16 M sodium thiosulfate.

After inactivation and neutralization, the fluids were divided into four aliquots. Each aliquot was adjuvanted with a different adjuvant as follows:

Formula A: 1.0 mL of inactivated harvest fluids plus 3.5 mL of PBS plus 0.5 mL of a Carbopol-based polymer adjuvant designated HAVLOGEN®.

Formula B: 1.0 mL of inactivated harvest fluids plus 3.25 mL PBS plus 0.75 mL of a polymer-based adjuvant designated POLYGEN®.

Formula C, 1.0 mL of inactivated harvest fluids plus 0.5 mL of HAVLOGEN® plus 3.5 mL of lipid-based adjuvant designated Bay R-1005.

Formula D: 1.0 mL of inactivated harvest fluids plus 0.5 mL of PBS plus 3.5 mL of MONTANIDE® 773.

Eighteen heifers ranging in age from 1.5 to 2.0 years of age were randomly separated into six groups. Group 1 heifers (No. U148, S85 and A184) did not receive a *Neospora caninum* vaccine. They served as contact controls and received uninfected MA104 Clone B cells. Group 2 heifers (No. A29, 13 and Z55) served as positive controls and received live *Neospora* tachyzoites ($3 \times 10^7$ intravenously and $8 \times 10^7$ intramuscularly). Group 3 heifers (No. 40, 1851, and A71) were vaccinated with three 5.0 mL doses of Formula A, administered subcutaneously at 4 week intervals. Group 4 heifers (No. 237, Y21, and U93) were vaccinated with three 5.0 mL doses of Formula B, administered subcutaneously at 4 week intervals. Group 5 heifers (No. Y6, X7, and 800) were vaccinated with three 5.0 mL doses of Formula C, administered subcutaneously at 4 week intervals. Group 6 heifers (No. A144, S74, and 5212) were vaccinated with three 5.0 mL doses of Formula D administered subcutaneously at 4 week intervals. All animals were bled at day 0 and bi-weekly thereafter.

Serum samples were analyzed for conversion to *Neospora* specific titers by use of an indirect fluorescent antibody (IFA) test. Table 3 shows the serological results. All of the vaccine preparations produced protective titer levels (>320) in the heifers. However, the polymer-based adjuvants appear to produce a better titer response than the oil-based adjuvant formulations. Since the contact control cattle remained serologically negative (within the test variation) for the duration of the experiment, it is clear that the titers produced in the vaccinated animals were not produced by shedding from the heifers injected with live Neospora tachyzoites but were a result of the vaccination.

had been removed and saved. Three batches of subunit DPBS re-suspended Neospora caninum were formulated to contain $1.2 \times 10^7$, $2.4 \times 10^7$ and $3.6 \times 10^7$ tachyzoites per dose, respectively. Three batches of supernatant re-suspended Neospora caninum were formulated to contain equivalent numbers of tachyzoites ($1.2 \times 10^7$, $2.4 \times 10^7$ and $3.6 \times 10^7$) per dose. All formulations were adjuvanted with HAVLOGEN® and

TABLE 3

IFA Titers of heifers vaccinated with Neospora caninum Vaccine Containing Four Different Adjuvants

| Treatment | Week 0 (Vacc) | Week 2 | Week 4 (Vacc) | Week 6 | Week 8 (Vacc) | Week 10 | Week 12 |
|---|---|---|---|---|---|---|---|
| Formula A | <80 | 320 | 160 | 160 | 160 | 320 | 320 |
|  | <80 | 160 | 80 | 160 | 160 | 640 | 320 |
|  | <80 | 320 | 80 | 160 | 320 | 640 | 160 |
| GMT | <80 | 254 | 101 | 160 | 202 | 508 | 254 |
| Formula B | <80 | 320 | 320 | 2560 | 1280 | 1280 | 1280 |
|  | <80 | 160 | 80 | 640 | 640 | 1280 | 640 |
|  | <80 | 320 | 160 | 640 | 640 | 1280 | 640 |
| GMT | <80 | 254 | 160 | 1016 | 806 | 1280 | 806 |
| Formula C | 80 | 640 | 160 | 1280 | 2560 | 2560 | 1280 |
|  | 80 | 320 | 160 | 1280 | 1280 | 2560 | 2560 |
|  | <80 | 160 | 160 | 2560 | 1280 | 1280 | 1280 |
| GMT | 19 | 320 | 160 | 1613 | 1613 | 2032 | 1613 |
| Formula D | <80 | 80 | 80 | 160 | 160 | 640 | 1280 |
|  | <80 | 80 | 160 | 160 | 320 | 1280 | 2560 |
|  | <80 | 80 | 160 | 640 | 640 | 1280 | 1280 |
| GMT | <80 | 80 | 127 | 254 | 320 | 1016 | 1613 |
| Live Tachys | <80 | 2560 | 5120 | 10240 | 5120 | 2560 | 1280 |
|  | <80 | 1280 | 20480 | 20480 | 20480 | 20480 | 20480 |
|  | <80 | 20480 | 20480 | 20480 | 20480 | 20480 | 5120 |
| GMT | <80 | 4064 | 12902 | 16255 | 12902 | 10240 | 5120 |
| Contact Controls | <80 | <80 | <80 | <80 | <80 | <80 | <80 |
|  | <80 | <80 | <80 | <80 | <80 | <80 | <80 |
|  | <80 | 80 | 80 | 160 | <80 | 80 | <80 |
| GMT | <80 | 4 | 4 | 5 | <80 | 4 | <80 |

GMT = Geometric Mean Titer
Vacc = Vaccination

Example 4

This experiment was conducted in order to determine the impact of Neospora caninum antigen quantity in the vaccines, and to evaluate a Neospora vaccine comprising subunit antigens. Also incorporated in this vaccine production process was the use of a "soft kill" technique which is defined as an inactivation process utilizing reduced quantities of inactivating agents and lower incubation temperatures and shorter inactivation times. For this experiment, the Neospora caninum was grown and processed in a manner similar to that described in EXAMPLE 3. The inactivation process was modified as follows. Binary ethylenimine was added to the harvested Neospora caninum to a final concentration of 0.01 M but was incubated at room temperature for only 24 hours after which it was neutralized by addition of sodium thiosulfate to a final concentration of 0.01 M. Subunits were obtained by removing aliquots of the inactivated tachyzoite fluids, centrifuging them at 3500 rpm for 15 minutes and decanting off the supernatant fluids. The Neospora tachyzoite pellets were re-suspended in Dulbecco's Phosphate Buffered Saline (DPBS) to produce a subunit vaccine containing only the tachyzoite antigens and not the exoantigens which are excreted by the tachyzoites into the medium. A second Neospora vaccine was prepared by re-suspending the Neospora tachyzoite pellet in the supernatant fluids which brought to a final 5.0 mL/dose concentration by addition of DPBS (to subunit vaccine) or supernatant fluid respectively.

These formulations were administered to Neospora seronegative heifers between the ages of 7 and 9 months of age. Six vaccine groups were comprised of five heifers each (n=5) and two control groups were comprised of three heifers each (n=3). Heifers in the experimental vaccine groups were each injected subcutaneously (SC) with 5.0 mL of one of the Neospora tachyzoite vaccine preparations and revaccinated four weeks later. Vaccine groups received the following vaccines:

Group 1 Subunit Neospora vaccine containing $1.2 \times 10^7$ Neospora tachyzoites with 10% HAVLOGEN®.

Group 2 Subunit Neospora vaccine containing $2.4 \times 10^7$ Neosporatachyzoites with 10% HAVLOGEN®.

Group 3 Subunit Neospora vaccine containing $3.6 \times 10^7$ Neosporatachyzoites with 10% HAVLOGEN®.

Group 4 Neospora vaccine containing $1.2 \times 10^7$ Neospora tachyzoites with 10% HAVLOGEN® and supernatant diluent.

Group 5 Neospora vaccine containing $2.4 \times 10^7$ Neospora tachyzoites with 10% HAVLOGEN® and supernatant diluent.

Group 6 Neospora vaccine containing $3.6 \times 10^7$ Neospora tachyzoites with 10% HAVLOGEN® and supernatant diluent.

Group 7 Contact Controls—These heifers received no vaccine.

Group 8 Positive Controls—These heifers received a challenge containing $5 \times 10^6$ live *Neospora* tachyzoites administered intravenously in a 5.0 mL dose and $3 \times 10^6$ live *Neospora* tachyzoites administered intramuscularly in a 5.0 mL dose.

All heifers were housed in the same lot, bled weekly for 7 weeks and all serum samples were tested for antibody titer specific for *Neospora caninum* using IFA. Additionally, the vaccines were evaluated for local reactivity by observing the sites of vaccination. Any local reactions were measured and recorded in centimeters. The serological titer responses of the heifers are shown in Table 4.

The results listed in Table 4 indicate that the vaccines containing the supernatant fluids added back to the *Neospora* pellet produce a slightly higher antibody response than the *Neospora* subunit vaccines. The antibody responses produced by the *Neospora caninum* vaccines containing the added-back supernatant also produced antibody responses which appear to be somewhat dose related. However, all of the vaccines were effective in producing protective levels of antibody in cattle.

None of the vaccines produced significant local reactions post vaccination. Therefore, all of the formulations could be considered acceptable commercial vaccine candidates.

TABLE 4

Geometric Mean IFA Titers of Heifers Vaccinated with Different Types of *Neospora* Vaccines Containing Increasing Concentrations of *Neospora* Tachyzoites

| Group | Days Post Vaccination | | | | | | | | | |
|---|---|---|---|---|---|---|---|---|---|---|
| | 0 | 7 | 14 | 21 | 28* | 35 | 42 | 49 | 56 | 64 |
| 1 | <40 | <80 | 80 | 320 | 160 | 2560 | 2560 | 2560 | 2560 | 1280 |
| | <40 | <80 | 320 | 320 | 320 | 2560 | 2560 | 2560 | 640 | 640 |
| | <40 | 320 | 640 | 640 | 320 | 1280 | 2560 | 640 | 320 | 1280 |
| | 80 | 320 | 640 | 640 | 640 | 640 | 1280 | 640 | 640 | 640 |
| | 40 | <80 | 160 | 80 | 80 | 320 | 2560 | 640 | 320 | 320 |
| GMT | 5 | 10 | 279 | 320 | 243 | 1114 | 2229 | 1114 | 640 | 735 |
| 2 | <40 | <80 | 160 | 160 | 160 | 320 | 5120 | 1280 | 320 | 320 |
| | <40 | 80 | 80 | 640 | 320 | 1280 | 5120 | 2560 | 2560 | 640 |
| | 80 | 160 | 640 | 320 | 320 | 640 | 640 | 320 | 320 | 320 |
| | 40 | 80 | 160 | 320 | 320 | 1280 | 1280 | 1280 | 1280 | 640 |
| | <40 | <80 | 320 | 160 | 160 | 320 | 320 | 320 | 160 | 320 |
| GMT | 5 | 16 | 211 | 279 | 243 | 640 | 1470 | 844 | 557 | 422 |
| 3 | <40 | 160 | 320 | 320 | 160 | 1280 | 1280 | 640 | 640 | 640 |
| | <40 | <80 | 640 | 160 | 160 | 640 | 1280 | 1280 | 320 | 1280 |
| | 40 | 320 | 1280 | 1280 | 640 | 2560 | 1280 | 1280 | 1280 | 320 |
| | 40 | <80 | <80 | 80 | 80 | 320 | 2560 | 640 | <80 | 640 |
| | 80 | 160 | 320 | 160 | 160 | 2560 | 5120 | 2560 | 640 | 320 |
| GMT | 11 | 24 | 153 | 243 | 184 | 114 | 1940 | 1114 | 176 | 557 |
| 4 | 40 | 320 | 1280 | 640 | 80 | 640 | 2560 | 2560 | 320 | 320 |
| | <40 | 160 | 320 | 640 | 160 | 2560 | 5120 | 5120 | 2560 | 640 |
| | 80 | 160 | 640 | 320 | 80 | 1280 | 1280 | 1280 | 640 | 640 |
| | 80 | 320 | 1280 | 1280 | 1280 | 2560 | 5120 | 2560 | 2560 | 1280 |
| | <40 | <80 | 160 | 160 | 160 | 1280 | 5120 | 1280 | 640 | 320 |
| GMT | 12 | 77 | 557 | 485 | 184 | 1470 | 3379 | 2229 | 970 | 557 |
| 5 | <40 | <80 | 160 | 320 | 160 | 1280 | 2560 | 2560 | 1280 | 1280 |
| | <40 | 160 | 160 | 640 | 160 | 2560 | 5120 | 1280 | 320 | 1280 |
| | <40 | <80 | 640 | 320 | 160 | 640 | 2560 | 1280 | 640 | 640 |
| | <40 | 160 | 640 | 160 | 320 | 2560 | 5120 | 1280 | 1280 | 1280 |
| | <40 | <80 | 160 | 80 | 80 | 160 | 1280 | 1280 | 640 | 160 |
| GMT | <40 | 7 | 279 | 243 | 160 | 970 | 2941 | 931 | 735 | 735 |

GMT = Geometric Mean Titer

Vacc = Vaccination

Although the invention has been described in detail in the foregoing for the purpose of illustration, it is to be understood that such detail is solely for that purpose and that variations can be made therein by those skilled in the art without departing from the spirit and scope of the invention except as it may be limited by the claim.

What is claimed is:

1. A method for protecting a fetus from fetal abortion caused by *Neospora caninum* infection in a pregnant bovine, comprising administering a *Neospora caninum* vaccine comprising inactivated *Neospora caninum* tachyzoites without excreted exoantigens in an effective amount to induce the production of antibodies to *Neospora caninum* in the pregnant mammal to a serological titer of at least 320 measured by indirect flourescent antibody tests.

2. The method of claim 1, wherein the *Neospora caninum* vaccine comprises *Neospora caninum* tachyzoites from tissue culture grown *Neospora caninum*.

3. The method of claim 1, wherein the *Neospora caninum* vaccine comprises an inactivating agent and an adjuvant.

4. The method according to claim 1, wherein the vaccine comprises inactivated *Neospora caninum* tachyzoites inactivated with an inactivating agent selected from the group consisting of formalin, beta-propiolactone, heat, binary ethylenimine, a detergent and combinations thereof.

5. The method according to claim 1, wherein the vaccine comprises an adjuvant and the adjuvant is selected from the group consisting of a polymer, an oil in water emulsion, a water-in-oil-in-water emulsion, a lipid, aluminum hydroxide, aluminum phosphate, aluminum sulfate, an immunomodulator and combinations thereof 6. The method of claim 1, wherein the *Neospora caninum* tachyzoites are inactivated by heat or freezing/thawing.

* * * * *